United States Patent [19]

Suzuki et al.

[11] Patent Number: 5,294,512
[45] Date of Patent: Mar. 15, 1994

[54] PYRENE COMPOUND, MANUFACTURING METHOD THEREFOR AND ELECTROPHOTOGRAPHIC PHOTORECEPTOR CONTAINING THE PYRENE COMPOUND

[75] Inventors: Tomoko Suzuki; Akira Kinoshita, both of Hino, Japan

[73] Assignee: Konica Corporation, Tokyo, Japan

[21] Appl. No.: 20,379

[22] Filed: Feb. 22, 1993

[30] Foreign Application Priority Data

Feb. 25, 1992 [JP] Japan ................... 4-038032

[51] Int. Cl.$^5$ ............................................. G03G 5/00
[52] U.S. Cl. ........................................ 430/78; 430/58; 430/76; 430/77; 548/301.7; 548/300.4; 546/27
[58] Field of Search ................ 430/78, 56, 57, 58, 430/76, 77; 534/561, 558; 548/324; 546/27

[56] References Cited

FOREIGN PATENT DOCUMENTS 0262029 5/1988 Japan .

*Primary Examiner*—Marion E. McCamish
*Assistant Examiner*—S. Rosasco
*Attorney, Agent, or Firm*—Finnegan, Henderson, Farabow, Garrett & Dunner

[57] ABSTRACT

The photoreceptor comprises a light-sensitive layer on a conductive support or a conductive layer. The light-sensitive layer containes a pyrene compounds.

9 Claims, 11 Drawing Sheets

PYRENE COMPOUND, MANUFACTURING METHOD THEREFOR AND ELECTROPHOTOGRAPHIC PHOTORECEPTOR CONTAINING THE PYRENE COMPOUND

BACKGROUND OF THE INVENTION

The present invention relates to novel pyrene compounds, a method for manufacturing them and an electrophotographic photoreceptor containing the pyrene compounds.

A study of photoconductive materials has recently been made actively, and the materials have been applied as a photoelectric conversion element such as a solar battery and an image sensor as well as an electrophotographic photoreceptor. Heretofore, inorganic materials have mainly been used for photoconductive materials. For example, an inorganic photoreceptor provided with a light-sensitive layer containing, as the main component, inorganic photoconductive materials such as selenium, zinc oxide or cadmium sulfide has been used widely. Such inorganic photoreceptor, however, has not necessarily been satisfactory on the points of characteristics required as an electrophotographic photoreceptor to be used in a copying machine such as photographic sensitivity, thermal stability, moisture resistance and durability. For example, the characteristic of selenium as an electrophotographic photoreceptor is easily deteriorated because the selenium is crystallized by heat or by finger print contamination. An electrophotographic photoreceptor employing cadmium sulfide, on the other hand, is inferior on the points of moisture resistance and durability, and an electrophotographic photoreceptor employing zinc oxide is also problematic on the point of durability. Furthermore, in recent years wherein environmental matters are taken seriously, an electrophotographic photoreceptor employing selenium or cadmium sulfide has disadvantages that restriction on manufacturing and handling thereof is strict on the point of its toxicity.

For improving the disadvantages of inorganic photoconductive materials, various organic photoconductive materials have drawn an attention to try to use it for a light-sensitive layer of an electrophotographic photoreceptor, and the study to use it have been conducted actively in recent years. For example, an organic photoreceptor provided with a light-sensitive layer containing polyvinylcarbazole and trinitrofluorenone is disclosed in Japanese Patent Examined Publication No. 10496/1975. However, this organic photoreceptor is not satisfactory on the points of photographic sensitivity and durability. Therefore, there has been developed an electrophotographic photoreceptor of a separated function type in which a carrier-generating function is carried out by one substance and a carrier-transport function is carried out by the other substance. In the field of such electrophotographic photoreceptor, it is expected to obtain an organic photoreceptor having high sensitivity and high durability, because desired characteristics are easily obtained due to wide selection of each material.

As a carrier-generating substance and a carrier-transport substance for such electrophotographic photoreceptor of a separated function type, there have been proposed various organic compounds. As a carrier-generating substance, photoconductive substances such as polycyclic quinone compounds represented by dibromoansanthrone, pyrylium compounds, eutectic crystal complexes of the pyrylium compounds, squarilium compounds, phthalocyanine compounds and azo compounds have been put to practical use.

For example, as an electrophotographic photoreceptor containing polycyclic quinone compounds in a light-sensitive layer, Japanese Patent Publication Open to Public Inspection Nos. 76933/1974, 75042/1975 and 180955/1988 (hereinafter referred to as Japanese Patent O.P.I. Publication) are known. However, these compounds are not necessarily satisfactory on the points of characteristics such as sensitivity or the like, and a range for selection of carrier-transport substances is limited, the compounds does not satisfy sufficiently the requirements of electrophotographic process in a wide range.

SUMMARY OF THE INVENTION

An object of the invention is to provide pyrene compounds especially useful as an organic photoconductive compound, manufacturing methods therefor and electrophotographic photoreceptors containing the pyrene compounds.

Pyrene compounds of the invention are those represented by the following general formula (1), (2), (3) or (4).

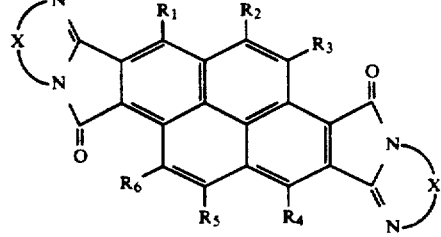

Formula (1)

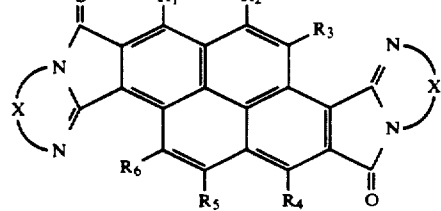

Formula (2)

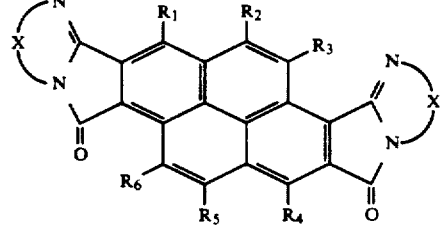

Formula (3)

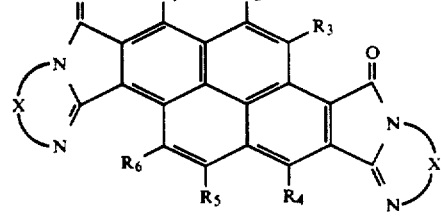

Formula (4)

In the formulas, X represents a substituted or unsubstituted divalent aromatic ring, $R_1$-$R_6$ each represent a hydrogen atom, a halogen atom, an alkyl group, an alkoxy group, an aryloxy group, an aralkyl group, or a substituted or unsubstituted aromatic group.

Preferable one represented by X includes a benzene ring, a naphthalene ring, an anthracene ring, a phenanthrene ring, a pyridine ring, a pyrimidine ring and an anthraquinone ring, and one especially preferable is represented by a benzene ring and a naphthalene ring. As a substituent of X, there may be given alkyl, alkoxy, aryl, aryloxy, acyl, acyloxy, amino, carbamoyl, halogen, nitro and cyano. Further, as $R_1$ and $R_4$, a substituted or unsubstituted aromatic group is preferable and a substituted or unsubstituted phenyl group is more preferable, while, as $R_2$, $R_3$, $R_5$ and $R_6$, a hydrogen atom and a halogen atom are preferable.

Further, another pyrene compound of the invention is a compound represented by the following formula (5).

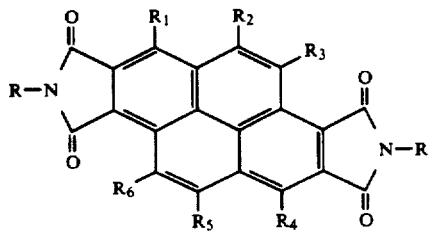

Formula (5)

In the formula, R represents a hydrogen atom, a substituted or unsubstituted alkyl group and a substituted or unsubstituted aromatic group, while $R_1$-$R_6$ represent a hydrogen atom, a halogen atom, an alkyl group, an alkoxy group, an aryloxy group, an aralkyl group and a substituted or unsubstituted aromatic group. As preferable one as R, a substituted or unsubstituted alkyl group having 1-5 carbon atoms and a substituted or unsubstituted phenyl group are given. As a substituent on an alkyl group, hydroxy, alkoxy, aryl, aryloxy, acyl and acyloxy are given. As a substituent on a phenyl group, alkyl, alkoxy, aryl, aryloxy, acyl, acyloxy, amino, carbamoyl, halogen, nitro and cyano are given. As $R_1$ and $R_4$, a substituted or unsubstituted aromatic ring residue is preferable and a substituted or unsubstituted phenyl group is more preferable. As $R_2$, $R_3$, $R_5$ and $R_6$, a hydrogen atom and a halogen atom are preferable.

Pyrene compounds represented by Formula (1), (2), (3) or (4) are manufactured through dehydrated condensation reaction between pyrene-1,2,6,7-tetracarboxylic acid bihydrate or its derivative represented by Formula (6) and diamino compounds represented by Formula (7). Incidentally, pyrene compounds represented by Formula (1), (2), (3) or (4) are structural isomers and they are produced in the aforementioned condensation reaction as mixtures which can be used without isolation.

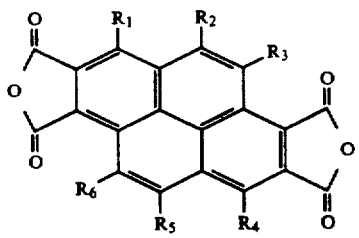

Formula (6)

Formula (7)

Formula (8)

$R_1$-$R_6$ in Formula (6) are the same as those in Formula (1), (2), (3) or (4).

Further, X in Formula (7) is the same as that in Formula (1), (2), (3) or (4)

Pyrene compounds represented by Formula (5) are manufactured through dehydrate condensation reaction between pyrene-1,2,6,7-tetracarboxylic dianhydride or its derivative represented by Formula (6) and amino compounds represented by Formula (8).

Incidentally, R in Formula (8) is the same as that in Formula (5).

The aforementioned manufacture synthesis is conducted at the temperature of 150°-250° C. while pyrene-1,2,6,7-tetracarboxylic dianhydride or its derivative and various types of diamino compounds or amino compounds in the mol ratio of 1;2-1;10, preferably of 1;2-1;3 are mixed and stirred in a non-reactive high boiling solvent, or preferably in a solvent of N-methylpyrrolidone, N,N-dimethylformamide, quinoline, or of α-chloronaphthalene. It is further possible to increase the rate of reaction by using a dehydrating catalyzer such as zinc chloride anhydride, zinc acetate anhydride, acetic acid and hydrochloric acid. It is effective to use a catalyzer in quantity of about 0.01-2 mol per one mol of acid anhydride.

Pyrene-1,2,6,7-tetracarboxylic dianhydride or its derivative which is a raw material compound for the invention can be obtained through a known method, for example, a method described on page 3293 of Volume 30 of Tetrahedron Journal (1974).

Pyrene compounds of the invention obtained in the aforementioned manner will be exemplified as follows, but the invention is not limited only to the exemplified compounds.

| Compound No. | R₁ | R₂ | R₃ | R₄ | R₅ | R₆ | X |
|---|---|---|---|---|---|---|---|
| 1 | H | H | H | H | H | H | 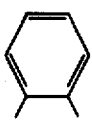 |
| 2 | H | H | H | H | H | H | 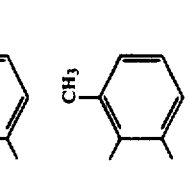 |
| 3 | H | H | H | H | H | H |  |
| 4 | H | H | H | H | H | H |  |
| 5 | H | H | H | H | H | H | 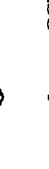 |
| 6 | H | H | H | H | H | H |  |
| 7 | H | H | H | H | H | H |  |
| 8 | H | H | H | H | H | H | (4-Cl-phenyl) |

-continued

| Compound No. | R₁ | R₂ | R₃ | R₄ | R₅ | R₆ | X |
|---|---|---|---|---|---|---|---|
| 9 | H | H | H | H | H | H | 4-bromophenyl |
| 10 | H | H | H | H | H | H | 4-nitrophenyl |
| 11 | H | H | H | H | H | H | 2,3-naphthyl |
| 12 | H | H | H | H | H | H | 1,8-naphthyl |
| 13 | H | H | H | H | H | H | 9,10-phenanthryl |
| 14 | H | H | H | H | H | H | 1,2-anthraquinonyl |

-continued
| Compound No. | R₁ | R₂ | R₃ | R₄ | R₅ | R₆ | X |
|---|---|---|---|---|---|---|---|
| 15 | H | H | H | H | H | H | 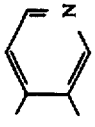 |
| 16 | H | H | H | H | H | H |  |
| 17 | H | H | CH₃ | H | H | CH₃ |  |
| 18 | H | H | OCH₃ | H | H | OCH₃ |  |
| 19 | H | H | Cl | H | H | Cl |  |
| 20 | H | H | Br | H | H | Br |  |
| 21 | H | CH₃ | H | H | CH₃ | H |  |
| 22 | H | OCH₃ | H | H | OCH₃ | H |  |

-continued
| Compound No. | R₁ | R₂ | R₃ | R₄ | R₅ | R₆ | X |
|---|---|---|---|---|---|---|---|
| 23 | H | 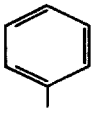 | H | H | 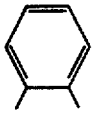 | H | phenyl |
| 24 | H | 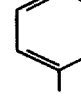 (–CH₃) | H | H | 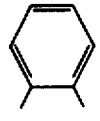 (–CH₃) | H | phenyl |
| 25 | H |  (–O–) | H | H | 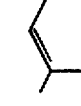 (–O–) | H | phenyl |
| 26 | H | Cl | H | H | Cl | H | phenyl |
| 27 | H | Br | H | H | Br | H | phenyl |
| 28 | H | Cl | Cl | H | Cl | Cl | phenyl |
| 29 | H | Br | Br | H | Br | Br | phenyl |
| 30 | H | Br | H | H | H | Br | phenyl |

-continued

| Compound No. | R₁ | R₂ | R₃ | R₄ | R₅ | R₆ | X |
|---|---|---|---|---|---|---|---|
| 31 | CH₃ | H | H | CH₃ | H | H | phenyl |
| 32 | CH₃ | H | H | CH₃ | H | H | 4-methylphenyl |
| 33 | CH₃ | H | H | CH₃ | H | H | 3,4-dimethylphenyl |
| 34 | CH₃ | H | H | CH₃ | H | H | 4-methoxyphenyl |
| 35 | CH₃ | H | H | CH₃ | H | H | 2-naphthyl |
| 36 | C₂H₅ | H | H | C₂H₅ | H | H | phenyl |
| 37 | C₂H₅ | H | H | C₂H₅ | H | H | 4-methylphenyl |
| 38 | C₂H₅ | H | H | C₂H₅ | H | H | 3,4-dimethylphenyl |

-continued

| Compound No. | R₁ | R₂ | R₃ | R₄ | R₅ | R₆ | X |
|---|---|---|---|---|---|---|---|
| 39 | C₂H₅ | H | H | C₂H₅ | H | H | 4,5-dimethoxyphenyl (2,3-di-OCH₃ benzene) |
| 40 | C₂H₅ | H | H | C₂H₅ | H | H | naphthyl |
| 41 | phenyl | H | H | phenyl | H | H | phenyl |
| 42 | phenyl | H | H | phenyl | H | H | 4-methylphenyl |
| 43 | phenyl | H | H | phenyl | H | H | 2,3-dimethylphenyl |
| 44 | phenyl | H | H | phenyl | H | H | 4,5-dimethylphenyl |
| 45 | phenyl | H | H | phenyl | H | H | 4-ethylphenyl |
| 46 | phenyl | H | H | phenyl | H | H | 4-methoxyphenyl |

-continued
| Compound No. | $R_1$ | $R_2$ | $R_3$ | $R_4$ | $R_5$ | $R_6$ | X |
|---|---|---|---|---|---|---|---|
| 47 |  | H | H |  | H | H |  |
| 48 |  | H | H |  | H | H |  |
| 49 |  | H | H |  | H | H |  |
| 50 |  | H | H |  | H | H |  |
| 51 |  | H | H |  | H | H |  |
| 52 |  | H | H |  | H | H |  |
| 53 |  | H | H |  | H | H |  |

-continued

| Compound No. | R₁ | R₂ | R₃ | R₄ | R₅ | R₆ | X |
|---|---|---|---|---|---|---|---|
| 54 | Ph | H | H | Ph | H | H | anthraquinone |
| 55 | Ph | H | H | Ph | H | H | pyrazine |
| 56 | Ph | H | H | Ph | H | H | pyridine |
| 57 | Ph | H | Cl | Ph | H | Cl | benzene |
| 58 | Ph | Br | Br | Ph | H | Br | benzene |
| 59 | Ph | Br | Br | Ph | Br | Br | benzene |
| 60 | Ph | Br | Br | Ph | Br | H | benzene |
| 61 | 4-CH₃-Ph | H | H | 4-CH₃-Ph | H | H | benzene |

-continued

| Compound No. | R₁ | R₂ | R₃ | R₄ | R₅ | R₆ | X |
|---|---|---|---|---|---|---|---|
| 62 | 4-CH₃-C₆H₄ | H | H | 4-CH₃-C₆H₄ | H | H | 3,4-(CH₃)-C₆H₃ |
| 63 | 4-CH₃-C₆H₄ | H | H | 4-CH₃-C₆H₄ | H | H | 3,4-(CH₃)₂-C₆H₂ |
| 64 | 4-CH₃-C₆H₄ | H | H | 4-CH₃-C₆H₄ | H | H | 3-OCH₃-C₆H₄ |
| 65 | 4-CH₃-C₆H₄ | H | H | 4-CH₃-C₆H₄ | H | H | 2-naphthyl |
| 66 | 4-OCH₃-C₆H₄ | H | H | 4-OCH₃-C₆H₄ | H | H | C₆H₄ |
| 67 | 4-OCH₃-C₆H₄ | H | H | 4-OCH₃-C₆H₄ | H | H | 3-CH₃-C₆H₄ |
| 68 | 4-OCH₃-C₆H₄ | H | H | 4-OCH₃-C₆H₄ | H | H | 3,4-(CH₃)₂-C₆H₂ |
| 69 | 4-OCH₃-C₆H₄ | H | H | 4-OCH₃-C₆H₄ | H | H | 3,4-(OCH₃)₂-C₆H₂ |

-continued

| Compound No. | R₁ | R₂ | R₃ | R₄ | R₅ | R₆ | X |
|---|---|---|---|---|---|---|---|
| 70 | 4-OCH₃-phenyl | H | H | 4-OCH₃-phenyl | H | H | 2-naphthyl |
| 71 | 2-naphthyl | H | H | 2-naphthyl | H | H | phenyl |
| 72 | 2-naphthyl | H | H | 2-naphthyl | H | H | 4-CH₃-phenyl |
| 73 | 2-naphthyl | H | H | 2-naphthyl | H | H | 3,4-(CH₃)₂-phenyl |
| 74 | 2-naphthyl | H | H | 2-naphthyl | H | H | 4-OCH₃-phenyl |
| 75 | 2-naphthyl | H | H | 2-naphthyl | H | H | 2-naphthyl |
| 76 | 2-naphthyl | H | H | 2-naphthyl | H | H | phenyl |
| 77 | 2-naphthyl | H | H | 2-naphthyl | H | H | 4-CH₃-phenyl |

-continued

| Compound No. | R₁ | R₂ | R₃ | R₄ | R₅ | R₆ | X |
|---|---|---|---|---|---|---|---|
| 78 | 2-naphthyl | H | H | H | H | H | 3,4-dimethylphenyl |
| 79 | 2-naphthyl | H | H | H | 2-naphthyl | H | 3,4-dimethoxyphenyl |
| 80 | 2-naphthyl | H | H | H | 2-naphthyl | H | 2-naphthyl |
| 81 | H | H | H | H | H | H | H |
| 82 | H | H | H | H | H | H | CH₃ |
| 83 | H | H | H | H | H | H | C₂H₅ |
| 84 | H | H | H | H | H | H | C₃H₇ |
| 85 | H | H | H | H | H | H | CH(CH₃)₂ |
| 86 | H | H | H | H | H | H | C₄H₉ |
| 87 | H | H | H | H | H | H | C₅H₁₁ |
| 88 | H | H | H | H | H | H | CH₂C(CH₃)₃ |
| 89 | H | H | H | H | H | H | CH₂CH₂CH₂OH |
| 90 | H | H | H | H | H | H | (CH₂)₃OCH₃ |
| 91 | H | H | H | H | H | H | phenyl |
| 92 | H | H | H | H | H | H | 3-methylphenyl |
| 93 | H | H | H | H | H | H | 4-methylphenyl |

-continued

| Compound No. | R₁ | R₂ | R₃ | R₄ | R₅ | R₆ | X |
|---|---|---|---|---|---|---|---|
| 94 | H | H | H | H | H | H | 3,5-dimethylphenyl |
| 95 | H | H | H | H | H | H | 2,4-dimethylphenyl |
| 96 | H | H | H | H | H | H | 3-ethylphenyl |
| 97 | H | H | H | H | H | H | 4-methoxyphenyl |
| 98 | H | H | H | H | H | H | 3,5-dimethoxyphenyl |
| 99 | H | H | H | H | H | H | 3,4,5-trimethoxyphenyl |

-continued

| Compound No. | R₁ | R₂ | R₃ | R₄ | R₅ | R₆ | X |
|---|---|---|---|---|---|---|---|
| 100 | H | H | H | H | H | H | −⟨3-Cl-C₆H₄⟩ |
| 101 | H | H | H | H | H | H | −CH₂−C₆H₅ |
| 102 | H | H | H | H | H | H | −CH₂−⟨4-OCH₃-C₆H₄⟩ |
| 103 | H | H | H | H | H | H | −CH₂CH₂−C₆H₅ |
| 104 | H | H | H | H | H | H | −CH₂CH₂−⟨3-CH₃-C₆H₄⟩ |
| 105 | H | H | H | H | H | H | −(CH₂)₃−C₆H₅ |
| 106 | H | H | Br | H | H | Br | C₆H₅ |
| 107 | H | Br | Br | H | Br | Br | C₆H₅ |

-continued

| Compound No. | $R_1$ | $R_2$ | $R_3$ | $R_4$ | $R_5$ | $R_6$ | X |
|---|---|---|---|---|---|---|---|
| 108 | H | phenyl | Br | H | phenyl | Br | phenyl |
| 109 | H | phenyl | Br | H | phenyl | Br | 3,5-dimethylphenyl |
| 110 | H | phenyl | Br | H | phenyl | Br | –CH$_2$–phenyl |
| 111 | CH$_3$ | H | H | CH$_3$ | H | H | phenyl |
| 112 | CH$_3$ | H | H | CH$_3$ | H | H | 3-methylphenyl |
| 113 | CH$_3$ | H | H | CH$_3$ | H | H | 3,5-dimethylphenyl |
| 114 | CH$_3$ | H | H | CH$_3$ | H | H | 4-methoxyphenyl |

-continued
| Compound No. | R₁ | R₂ | R₃ | R₄ | R₅ | R₆ | X |
|---|---|---|---|---|---|---|---|
| 115 | CH₃ | H | H | CH₃ | H | H |  |
| 116 | C₂H₅ | H | H | C₂H₅ | H | H |  |
| 117 | C₂H₅ | H | H | C₂H₅ | H | H | 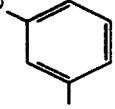 |
| 118 | C₂H₅ | H | H | C₂H₅ | H | H | 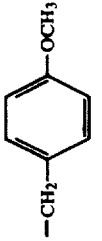 |
| 119 | C₂H₅ | H | H | C₂H₅ | H | H | 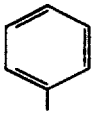 |
| 120 | C₂H₅ | H | H | C₂H₅ | H | H | 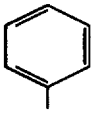 |
| 121 | C₂H₅ | H | H | 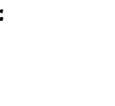 | H | H | H |

-continued
| Compound No. | R₁ | R₂ | R₃ | R₄ | R₅ | R₆ | X |
|---|---|---|---|---|---|---|---|
| 122 |  | H | H |  | H | H | CH₃ |
| 123 |  | H | H |  | H | H | C₂H₅ |
| 124 |  | H | H |  | H | H | C₃H₇ |
| 125 |  | H | H |  | H | H | CH(CH₃)₂ |
| 126 |  | H | H |  | H | H | C₄H₉ |
| 127 |  | H | H |  | H | H | C₅H₁₁ |
| 128 |  | H | H |  | H | H | CH₂C(CH₃)₃ |
| 129 |  | H | H |  | H | H | CH₂CH₂CH₂OH |

-continued

| Compound No. | R₁ | R₂ | R₃ | R₄ | R₅ | R₆ | X |
|---|---|---|---|---|---|---|---|
| 130 | Ph | H | H | Ph | H | H | (CH₂)₃OCH₃ |
| 131 | Ph | H | H | Ph | H | H | Ph |
| 132 | Ph | H | H | Ph | H | H | 3-CH₃-C₆H₄ |
| 133 | Ph | H | H | Ph | H | H | 4-CH₃-C₆H₄ |
| 134 | Ph | H | H | Ph | H | H | 3,5-(CH₃)₂-C₆H₃ |
| 135 | Ph | H | H | Ph | H | H | 2,4-(CH₃)₂-C₆H₃ |
| 136 | Ph | H | H | Ph | H | H | 3-C₂H₅-C₆H₄ |

-continued

| Compound No. | R₁ | R₂ | R₃ | R₄ | R₅ | R₆ | X |
|---|---|---|---|---|---|---|---|
| 137 | C₆H₅ | H | H | C₆H₅ | H | H | 4-OCH₃-C₆H₄ |
| 138 | C₆H₅ | H | H | C₆H₅ | H | H | 3,5-(OCH₃)₂-C₆H₃ |
| 139 | C₆H₅ | H | H | C₆H₅ | H | H | 2,3,4-(OCH₃)₃-C₆H₂ |
| 140 | C₆H₅ | H | H | C₆H₅ | H | H | 3-Cl-C₆H₄ |
| 141 | C₆H₅ | H | H | C₆H₅ | H | H | —CH₂—C₆H₅ |
| 142 | C₆H₅ | H | H | C₆H₅ | H | H | —CH₂—C₆H₄-4-OCH₃ |
| 143 | C₆H₅ | H | H | C₆H₅ | H | H | —CH₂CH₂—C₆H₅ |

-continued

| Compound No. | R₁ | R₂ | R₃ | R₄ | R₅ | R₆ | X |
|---|---|---|---|---|---|---|---|
| 144 | phenyl | H | H | phenyl | H | H | -CH₂CH₂-(3-methylphenyl) |
| 145 | phenyl | H | H | phenyl | H | H | -CH₂CH₂-(2-pyridyl) |
| 146 | phenyl | H | Br | phenyl | H | Br | -(CH₂)₃-phenyl |
| 147 | phenyl | H | Cl | phenyl | H | Cl | phenyl |
| 148 | phenyl | Cl | Br | phenyl | H | Br | phenyl |
| 149 | phenyl | Br | Br | phenyl | H | Br | 3-methylphenyl |
| 150 | phenyl | H | Br | phenyl | H | Br | 3-methylphenyl |
| 151 | 4-methylphenyl | H | H | 4-methylphenyl | H | H | n-C₃H₇ |

-continued
| Compound No. | $R_1$ | $R_2$ | $R_3$ | $R_4$ | $R_5$ | $R_6$ | X |
|---|---|---|---|---|---|---|---|
| 152 | 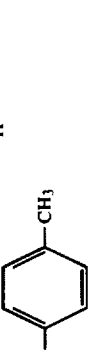 | H | H |  | H | H | $CH_2CH_2CH_2OH$ |
| 153 | 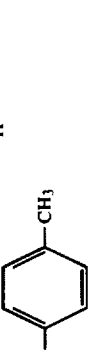 | H | H |  | H | H | 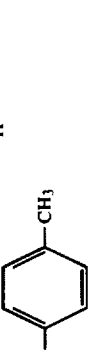 |
| 154 |  | H | H |  | H | H | 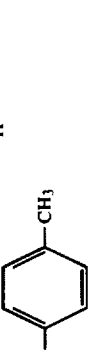 |
| 155 |  | H | H |  | H | H | 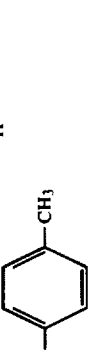 |
| 156 |  | H | H |  | H | H | 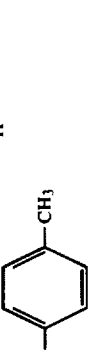 |
| 157 |  | H | H |  | H | H | 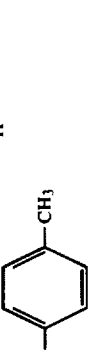 |
| 158 |  | H | H |  | H | H | |

-continued

| Compound No. | R₁ | R₂ | R₃ | R₄ | R₅ | R₆ | X |
|---|---|---|---|---|---|---|---|
| 159 | 4-OCH₃-C₆H₄ | H | H | 4-OCH₃-C₆H₄ | H | H | 4-OCH₃-C₆H₄ |
| 160 | 4-OCH₃-C₆H₄ | H | H | 4-OCH₃-C₆H₄ | H | H | -CH₂-C₆H₅ |
| 161 | 2-naphthyl | H | H | 2-naphthyl | H | H | C₃H₇ |
| 162 | 2-naphthyl | H | H | 2-naphthyl | H | H | C₅H₁₁ |
| 163 | 2-naphthyl | H | H | 2-naphthyl | H | H | CH₂CH₂CH₂OH |
| 164 | 2-naphthyl | H | H | 2-naphthyl | H | H | C₆H₅ |
| 165 | 2-naphthyl | H | H | 2-naphthyl | H | H | 3,5-(OCH₃)₂-C₆H₃ |
| 166 | 1-naphthyl | H | H | 1-naphthyl | H | H | C₆H₅ |

-continued

| Compound No. | R₁ | R₂ | R₃ | R₄ | R₅ | R₆ | X |
|---|---|---|---|---|---|---|---|
| 167 | 1-naphthyl | H | H | 1-naphthyl | H | H | 3-methylphenyl |
| 168 | 1-naphthyl | H | H | 1-naphthyl | H | H | 3,4-dimethylphenyl |
| 169 | 1-naphthyl | H | H | 1-naphthyl | H | H | 4-methoxyphenyl |
| 170 | 1-naphthyl | H | H | 1-naphthyl | H | H | —CH₂—phenyl |

DETAILED DESCRIPTION OF THE PREFERRED EMBODIMENTS

How pyrene compounds of the invention are used for an electrophotographic photoreceptor will be explained as follows.

Figure 1:
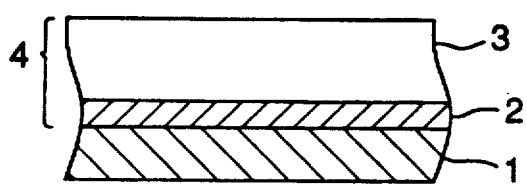
FIGS. 1(a) through 1(f) are sectional views of a concrete example for a layer structure in a photoreceptor of the invention.
Figure 1:
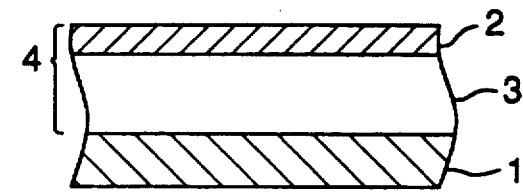
Figure 1:
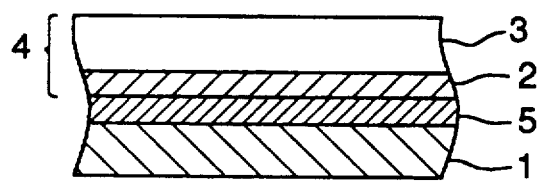
Figure 1:
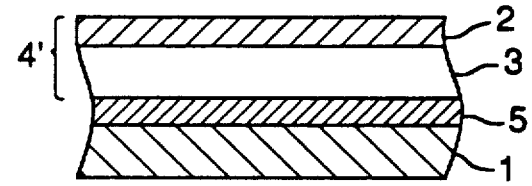
Figure 1:
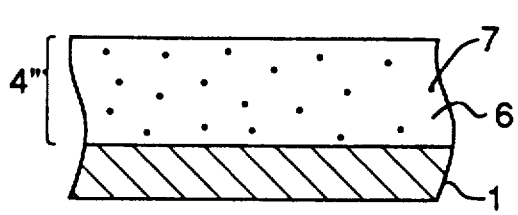
Figure 1:
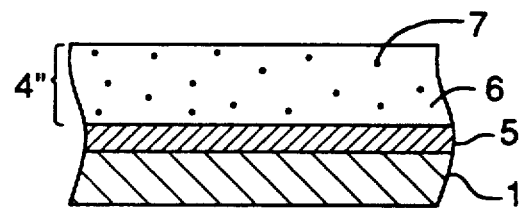

As a structure of a photoreceptor, there are known various types of them any one of which can be applied to a photoreceptor of the invention. However, it is preferable to employ a photoreceptor of a separated-function type such as one of a lamination type or one of a dispersed type. In this case, a structure usually comes under those shown in FIG. 1(a) FIG. 1(f). In the layer structure shown in the FIG. 1(a), carrier-generating layer 2 is formed on conductive support 1 and carrier-transport layer 3 is laminated on the carrier-generating layer to form light-sensitive layer 4, while in the FIG. 1(b), the carrier-generating layer 2 and the carrier-transport layer 3 are arranged reversely compared with an arrangement in the FIG. 1(a) to form light-sensitive layer 4'. In FIG. 1(c), intermediate layer 5 is provided between light-sensitive layer 4 having the layer structure shown in FIG. 1(a) and conductive support 1, while in FIG. 1(d), intermediate layer 5 is provided between light-sensitive layer having the layer structure shown in FIG. 1(b) and conductive support 1. In the layer structure shown in FIG. 1(e), light-sensitive layer 4" containing carrier-generating substances 6 and carrier-transport substances 7 is formed, while in FIG. 1(f), intermediate layer 5 is formed between the light-sensitive layer 4" and conductive support 1.

In the invention, it is also possible to use other carrier-generating substances in combination with the aforementioned pyrene compounds. Such carrier-generating substance includes phthalocyanine pigment, azo pigment, anthraquinone pigment, perylene pigment, polycyclic quinone pigment and squarilium pigment.

As a carrier-transport substance in a photoreceptor of the invention, various types of them may be used, and typical ones, for example, include a nitrogen-containing heterocycle nuclear represented by oxazoles, oxadiazoles, thiazoles, thiadiazoles and imidazoles and compounds having its condensed ring nuclear therefrom, polyarylalkane compounds, pyrazoline compounds, hydrazone compounds, triarylamine compounds, styryl compounds, styryltriphenylamine compounds, β-phenylstyryltriphenylamine compounds, butadiene compounds, hexatriene compounds, carbazole compounds and condensed polycyclic compounds.

A carrier-generating layer is formed either by coating a liquid wherein carrier-generating substances are dispersed to be fine particles in a relevant dispersant independently or in combination with binders and additives or by vacuum-evaporating carrier-generating substances. In the case of the former, a dispersing equipment such as a super-sonic dispersing equipment, a ball mill, a sand mill and a homomixer may be used as a dispersing means. For a carrier-transport layer, it is an effective method to coat a solution wherein carrier-transport substances are dissolved independently or in combination with binders and additives.

As a solvent or a dispersant to be used for forming a light-sensitive layer, ordinary ones may be used widely. For example, butylamine, ethylenediamine, N,N-dimethylformamide, acetone, methylethylketone, cyclohexanone, tetrahydrofuran, dioxane, ethyl acetate, butyl acetate, methylcellosolve, ethylcellosolve, ethyleneglycoldimethylether, toluene, xylene, acetophenone, chloroform, dichloromethane, dichloroethane, trichloroethane, methanol, ethanol, propanol and butanol may be given.

When a binder is used for forming a carrier-generating layer, or a carrier-transport layer, any binders may be selected for use. However, a high molecular polymer which is hydrophobic and is capable of forming a film is preferable. Examples of the polymer are shown below, but the invention is not limited to them.

Polycarbonate
Polycarbonate Z resin
Acrylic resin
Methacrylic resin
Polyvinyl chloride
Polyvinylidene chloride
Polystyrene
Styrene-butadiene copolymer
Polyvinyl acetate
Polyvinylformal
Polyvinylbutyral
Polyvinylacetal
Polyvinylcarbazole
Styrene-alkyd resin
Silicone resin
Silicone-alkyd resin
Polyester
Phenol resin
Polyurethane
Epoxy resin
Vinylidene chloride-acrylonitrile co-polymer
Vinyl chloride-vinyl acetate co-polymer
Vinyl chloride-vinyl acetate-maleic anhydride co-polymer It is preferable that a rate of carrier-generating substances to binders is 10–600% by weight, and a rate of 50–400% by weight is more preferable. It is preferable that a rate of carrier-transport substances to binders is 10–500% by weight. The thickness of a carrier-generating layer is 0.01–20 μm in which a range of 0.05–5 μm is preferable. The thickness of a carrier-transport layer is 1–100 μm in which a range of 5–30 μm is preferable.

It is possible to cause the light-sensitive layer mentioned above to contain electron-accepting substances for the purpose of improving its photographic sensitivity, reducing its residual potential or reducing its fatigue in repeated use. As examples of the electron-accepting substance, there may be given succinic anhydride, maleic anhydride, dibromosuccinic anhydride, phthalic anhydride, tetrachlorophthalic anhydride, tetrabromophthalic anhydride, 3-nitrophthalic anhydride, 4-nitrophthalic anhydride, pyromellitic anhydride, mellitic anhydride, tetracyanoethylene, tetracyanoquinodimethane, o-dinitrobenzene, m-dinitrobenzene, 1,3,5-trinitrobenzene, p-nitrobenzonitrile, picryl chloride, quinone chloroimide, chloranyl, bromanyl, dichlorodicyano-p-benzoquinone, anthraquinone, dinitroanthraquinone, 9-fluorenylidenemalonodinitrile, polynitro-9-fluorenylidenemalonodinitrile, picric acid, o-nitrobenzoic acid, p-nitrobenzoic acid, 3,5-dinitrobenzoic acid, pentafluorobenzoic acid, 5-nitrosalicylic acid, 3,5-dinitrosalicylic acid, phthalic, mellitic acid and other compounds having a great electron-affinity. It is preferable that a rate of adding electron-accepting substances is 0.01–200 for 100 in weight of carrier-generating substances, and a rate of 0.1–100 is more preferable.

It is further possible to cause the aforementioned light-sensitive layer to contain anti-degradation agents such as antioxidant and light-stabilizer for the purpose of improving preservability, durability and anti-environment-dependence properties. As a compound to be used for that purpose, a chlomanol derivative such as tocopherol and its etherized compound or esterized compound, a polyarylalkane compound, a hydroquinone derivative and its monoetherized compound and diehterized compound, a benzophenone derivative, a benztriazole derivative, a thioether compound, phosphonic acid ester, phosphorous ester, a phenylenediamine derivative, a phenol compound, a hindered phenol compound, a straight chain compound, a cyclic amine compound and a hindered amine compound, for example, are effective. As a concrete example of a compound which is especially effective, there may be given hindered phenol compounds such as "IRGANOX 1010", "IRGANOX 565" (made by Ciba Ltd), "Sumilizer BHT" and "Sumilizer MDP" (made by SUMITOMO KAGAKU KOGYO CO.) and hindered amine compounds such as "SANOL LS2626", "SANOL LS622LD" (made by SANKYO CO.).

As a binder to be used for an interlayer or a protective layer, it is possible to use those cited to be used for the above-mentioned carrier-generating layer and carrier-transport layer. In addition to the above, polyamide resin, nylon resin, ethylene type resin such as ethylene-vinyl acetate co-polymer, ethylene-vinyl acetate-maleic anhydride co-polymer and ethylene-vinyl acetate-methacrylic acid co-polymer, polyvinylalcohol and cellulose derivatives are effective.

As a conductive support, it is possible to use, in addition to a metal sheet and a metal drum, the dielectric compounds such as conductive polymer and indium oxide, or those wherein a metal foil of aluminum or palladium is provided on a substrate made of paper or plastic film through a means of coating, evaporating or laminating.

EXAMPLES

There will be given examples as follows to which the invention is not limited.

EXAMPLE 1

Figure 2:
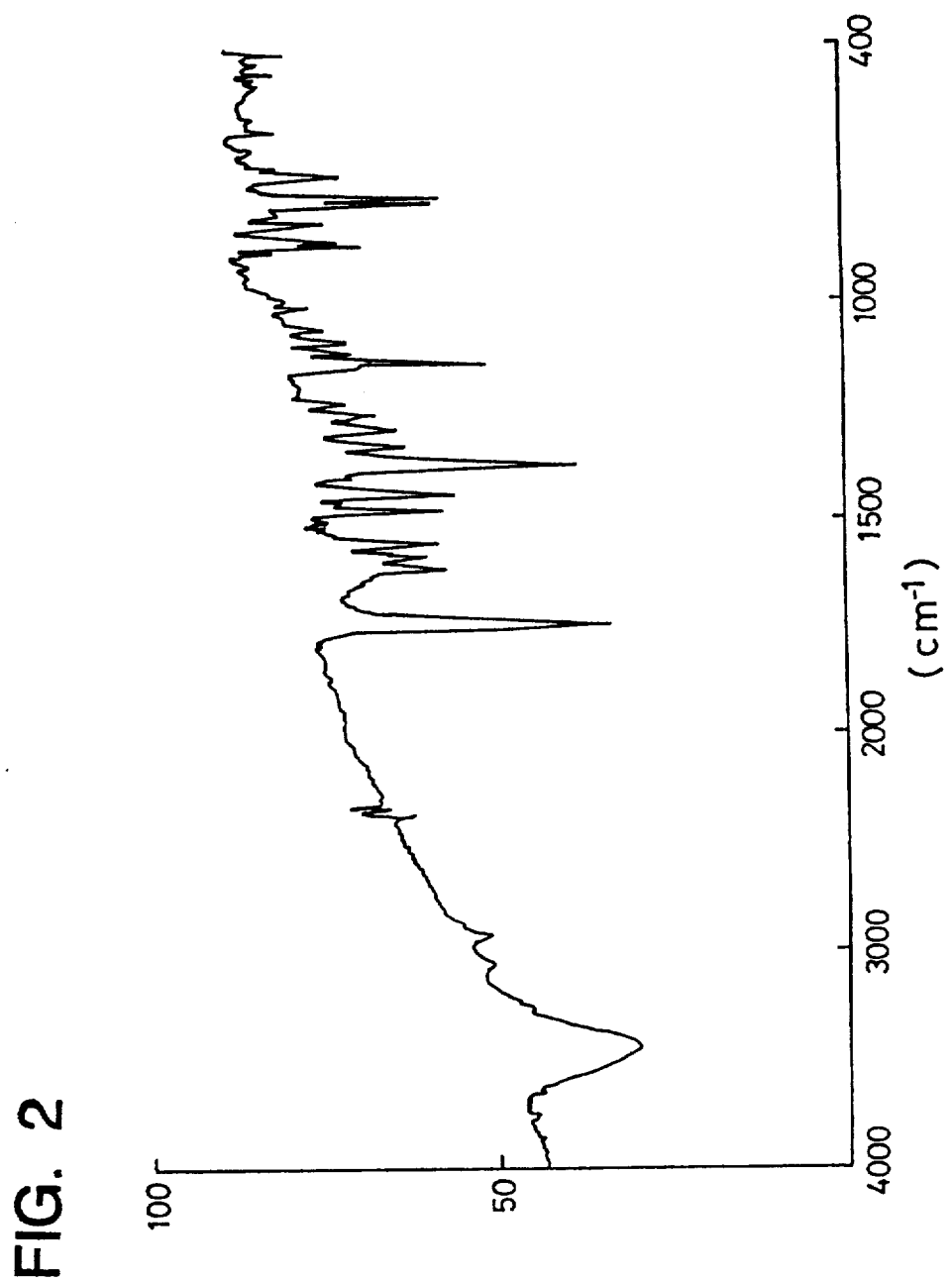
FIG. 2 is a diagram of infrared spectrum obtained through a KBr tablet method for pyrene compounds obtained in Example 1.

For two hours, 3,8-diphenylpyrene-1,2,6,7-tetracarboxylic dianhydride in quantity of 2.5 g (0.005 mol), o-phenylenediamine in quantity of 1.6 g (0.015 mol) and zincchloride anhydride in quantity of 0.1 g (0.001 mol) were refluxed in quinoline in quantity of 50 ml, and crystals precipitated were isolated by filtration. The crystals were dried after being washed with acetone and methanol, and products in quantity of 2.8 g (88%) were obtained. The products were refined through sublimation. An infrared absorption spectrum therefor is shown in FIG. 2. It was observed that infrared absorption at $v=1840$, 1770 cm$^{-1}$ disappeared and that at $v=1740$ cm$^{-1}$ appeared newly, and bis (benzimidazole) diphenyl pyrene (Exemplified compound No. 41) was synthesized by molecular ion peak (m/e=638) of FD-mass-spectrum. This is considered to be a mixture of three kinds of structural isomers shown below.

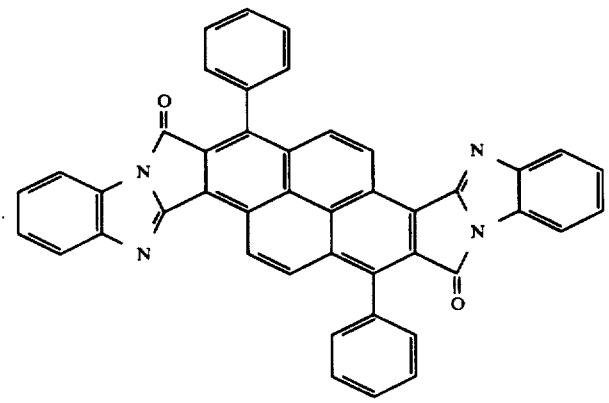

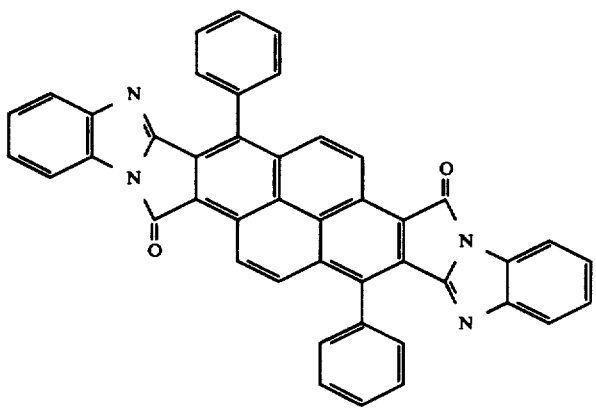

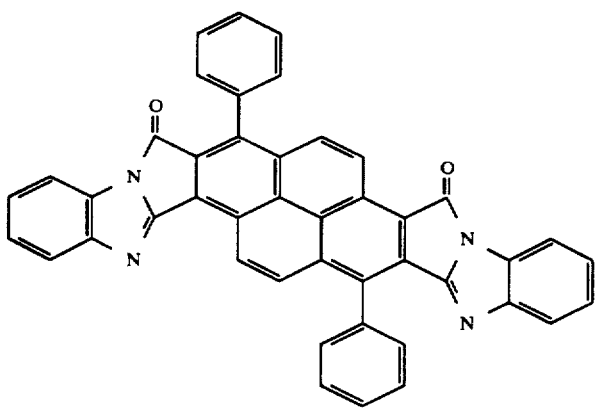

EXAMPLES 2-5

Various types of pyrene compounds were prepared in the same manner as in Example 1 except that o-phenylenediamine in Example 1 was replaced by diamino compound in Table 1. The results of them are shown in Table 1. Infrared absorption spectra of these pyrene compounds are shown in FIGS. 3-6.

TABLE 1

Figure 3:
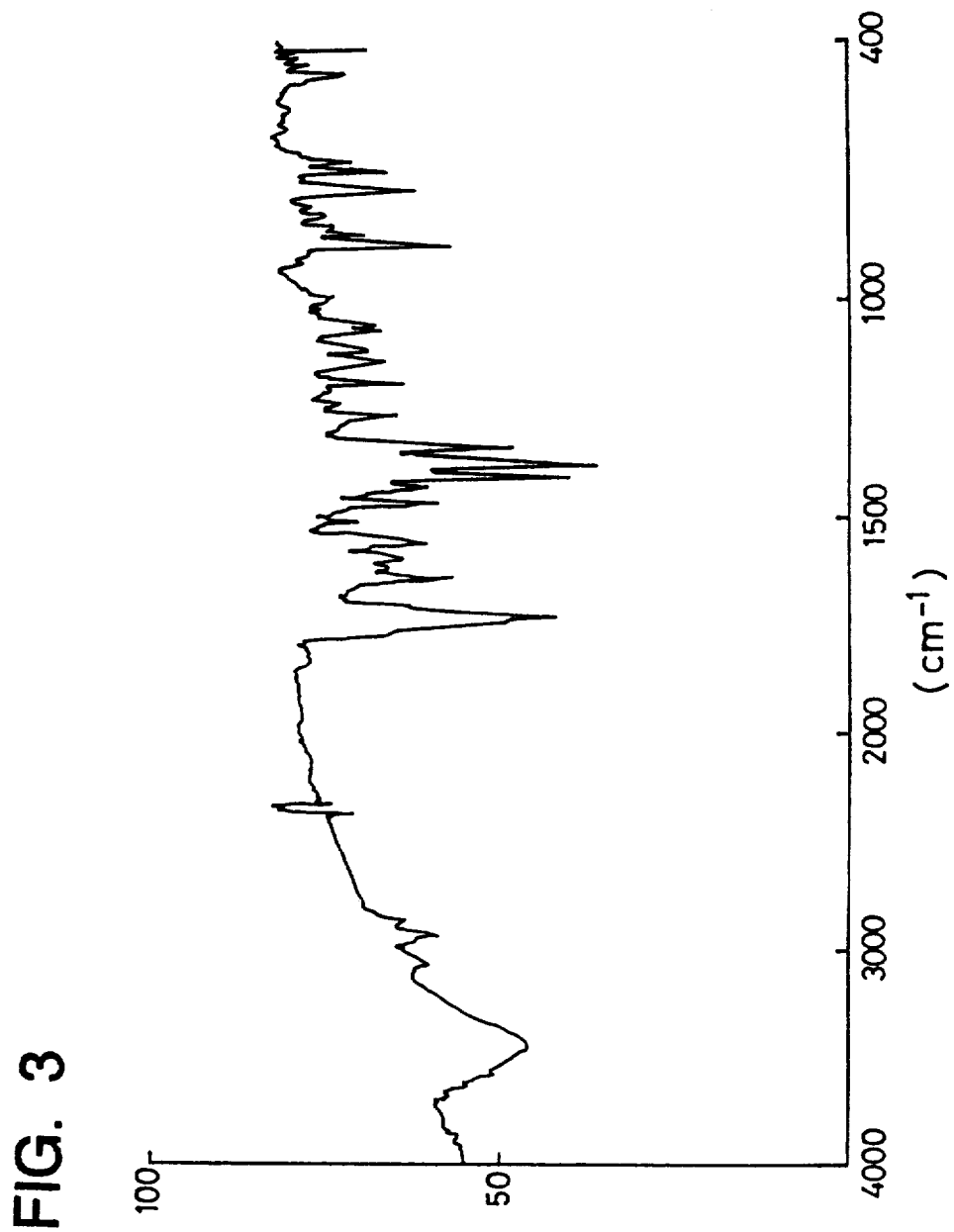
FIG. 3 is a diagram of infrared spectrum obtained through a KBr tablet method for pyrene compounds obtained in Example 2.
Figure 4:
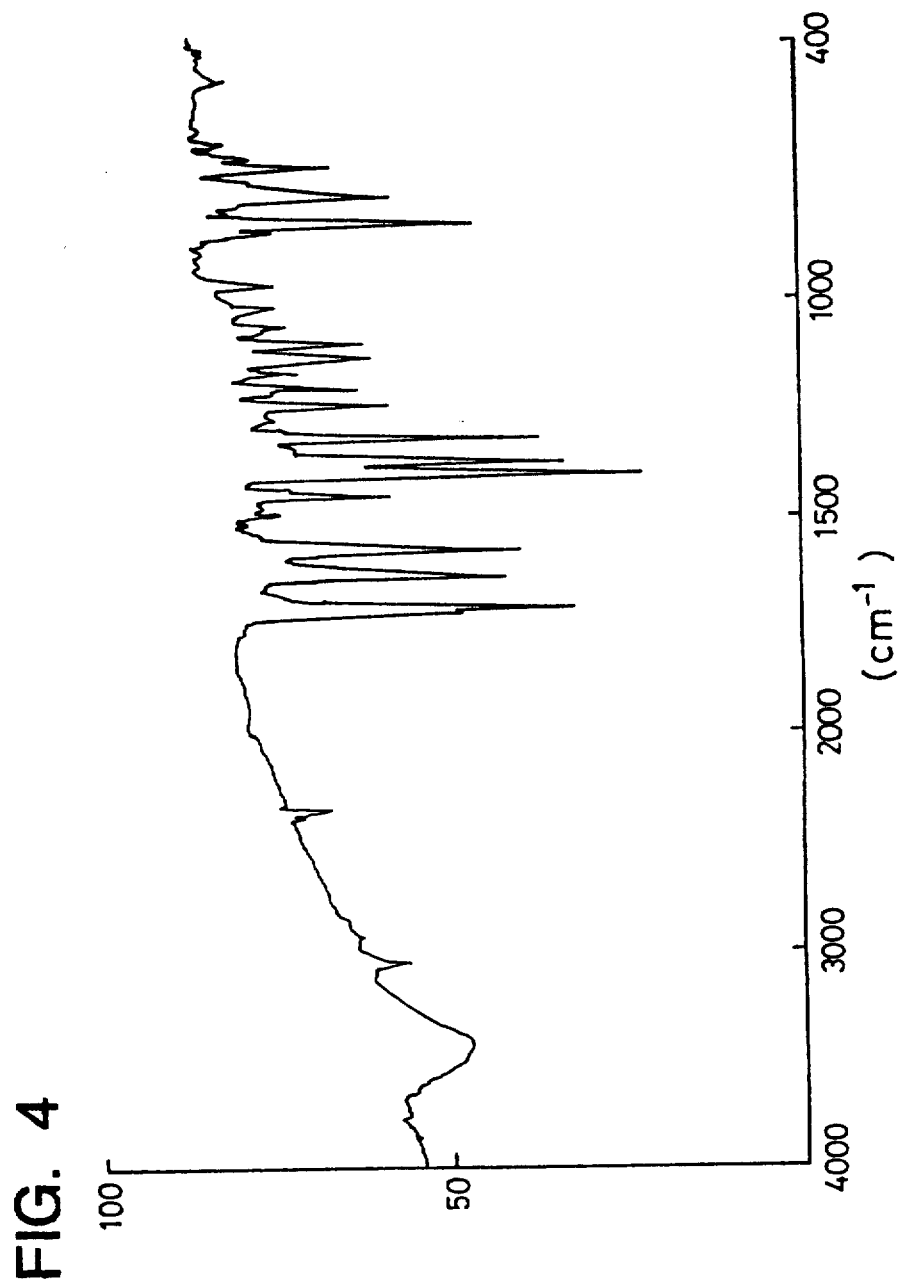
FIG. 4 is a diagram of infrared spectrum obtained through a KBr tablet method for pyrene compounds obtained in Example 3.
Figure 5:
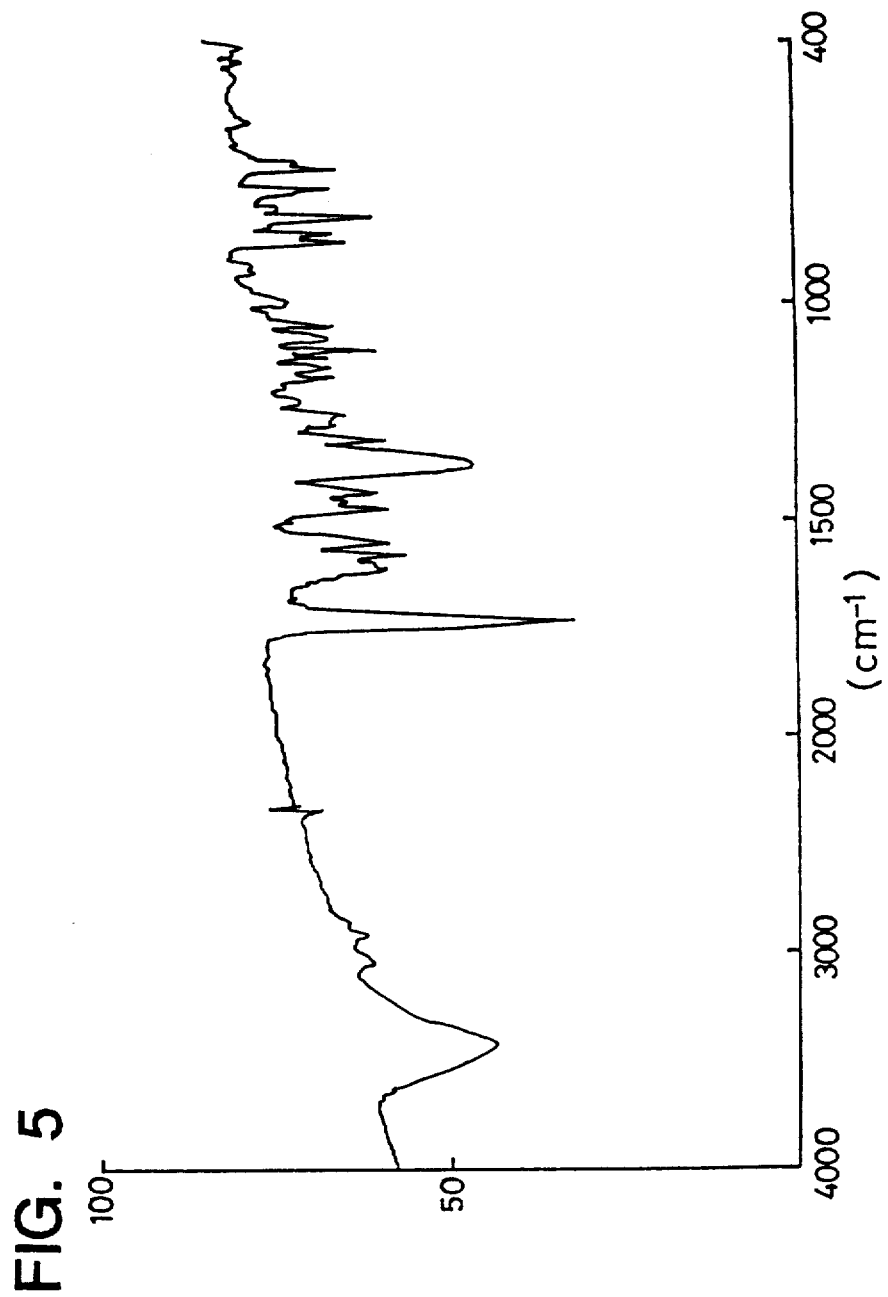
FIG. 5 is a diagram of infrared spectrum obtained through a KBr tablet method for pyrene compounds obtained in Example 4.

| Example No. | Diamino compound | Pyrene compound No. | Yield (%) | Infrared absorption spectrum (KBr tablet method) |
|---|---|---|---|---|
| 1 | ⌬-NH₂, NH₂ (o-phenylenediamine) | 41 | 88 | FIG. 2 |
| 2 | CH₃-⌬-NH₂, NH₂ | 42 | 78 | FIG. 3 |
| 3 | CH₃-⌬(CH₃)-NH₂, NH₂ | 44 | 86 | FIG. 4 |
| 4 | naphthalene-NH₂, NH₂ | 51 | 89 | FIG. 5 |

TABLE 1-continued

Figure 6:
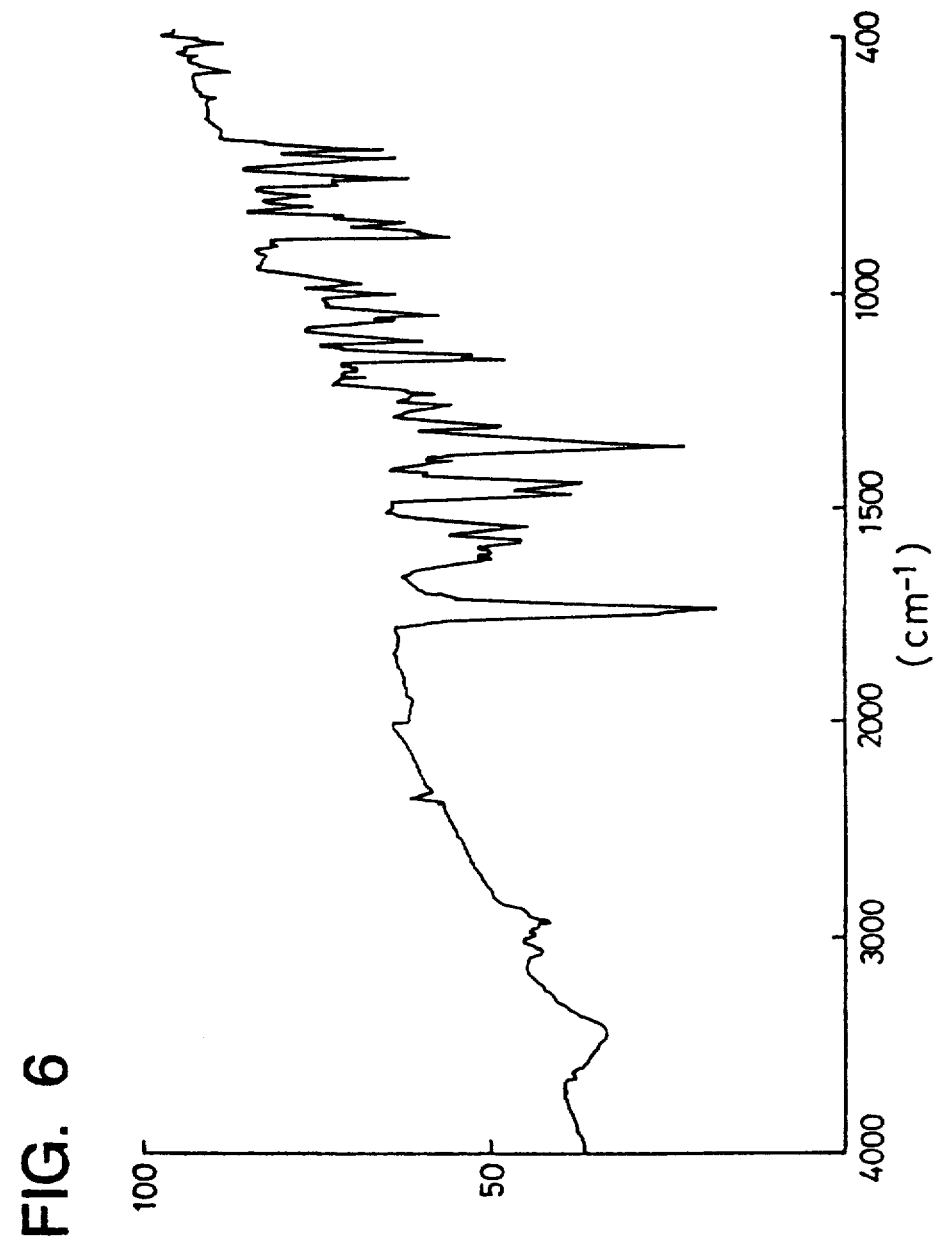
FIG. 6 is a diagram of infrared spectrum obtained through a KBr tablet method for pyrene compounds obtained in Example 5.

| Example No. | Diamino compound | Pyrene compound No. | Yield (%) | Infrared absorption spectrum (KBr tablet method) |
|---|---|---|---|---|
| 5 | naphthalene-1,5-diamine (structure: naphthalene with two -NH$_2$ groups) | 52 | 92 | FIG. 6 |

EXAMPLES 6-10

Various types of pyrene compounds were prepared in the same manner as in Example 1 except that o-phenylenediamine in Example 1 was replaced by amino compound in Table 2. The results of them are shown in Table 2. Infrared absorption spectra of these pyrene compounds are shown in FIGS. 7-11.

TABLE 2

Figure 7:
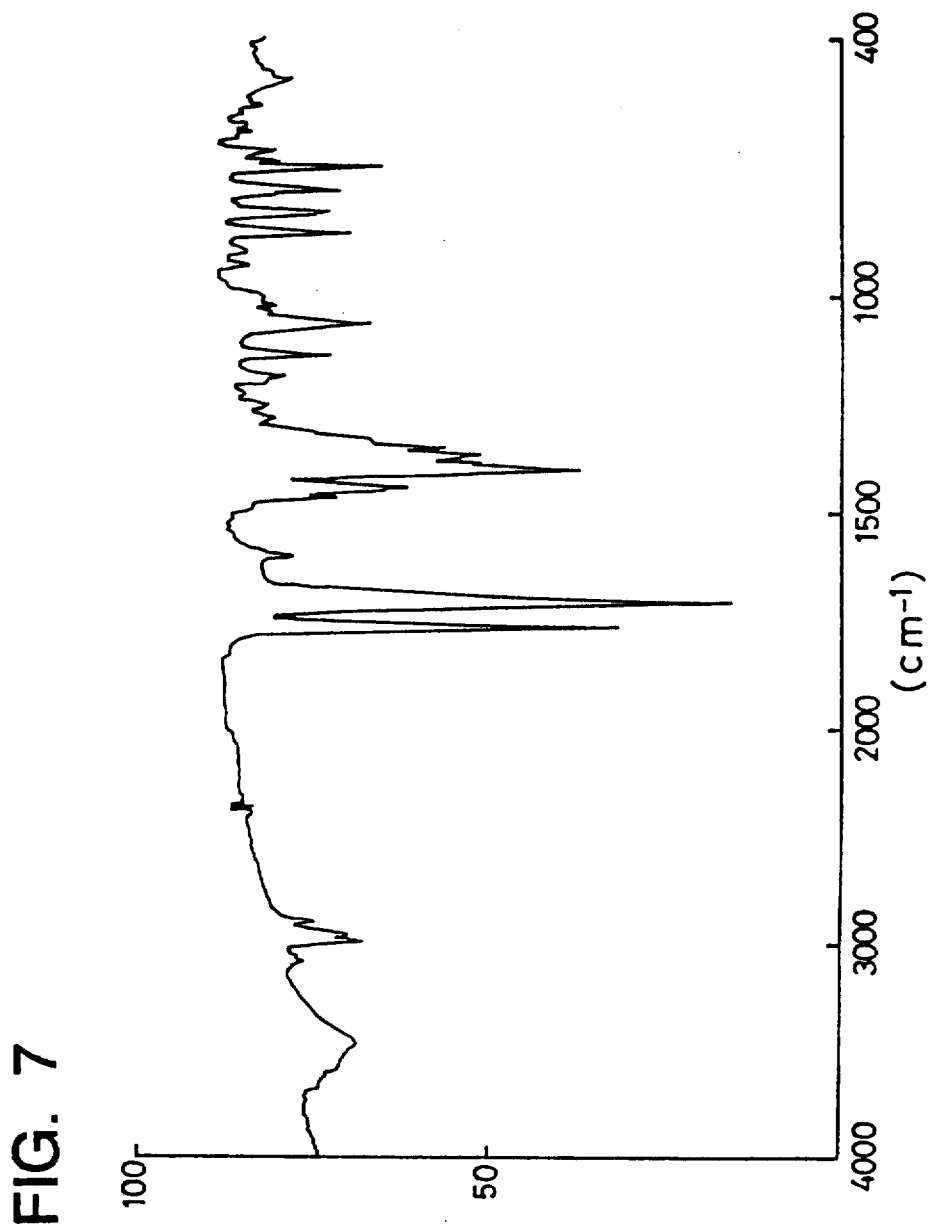
FIG. 7 is a diagram of infrared spectrum obtained through a KBr tablet method for pyrene compounds obtained in Example 6.
Figure 8:
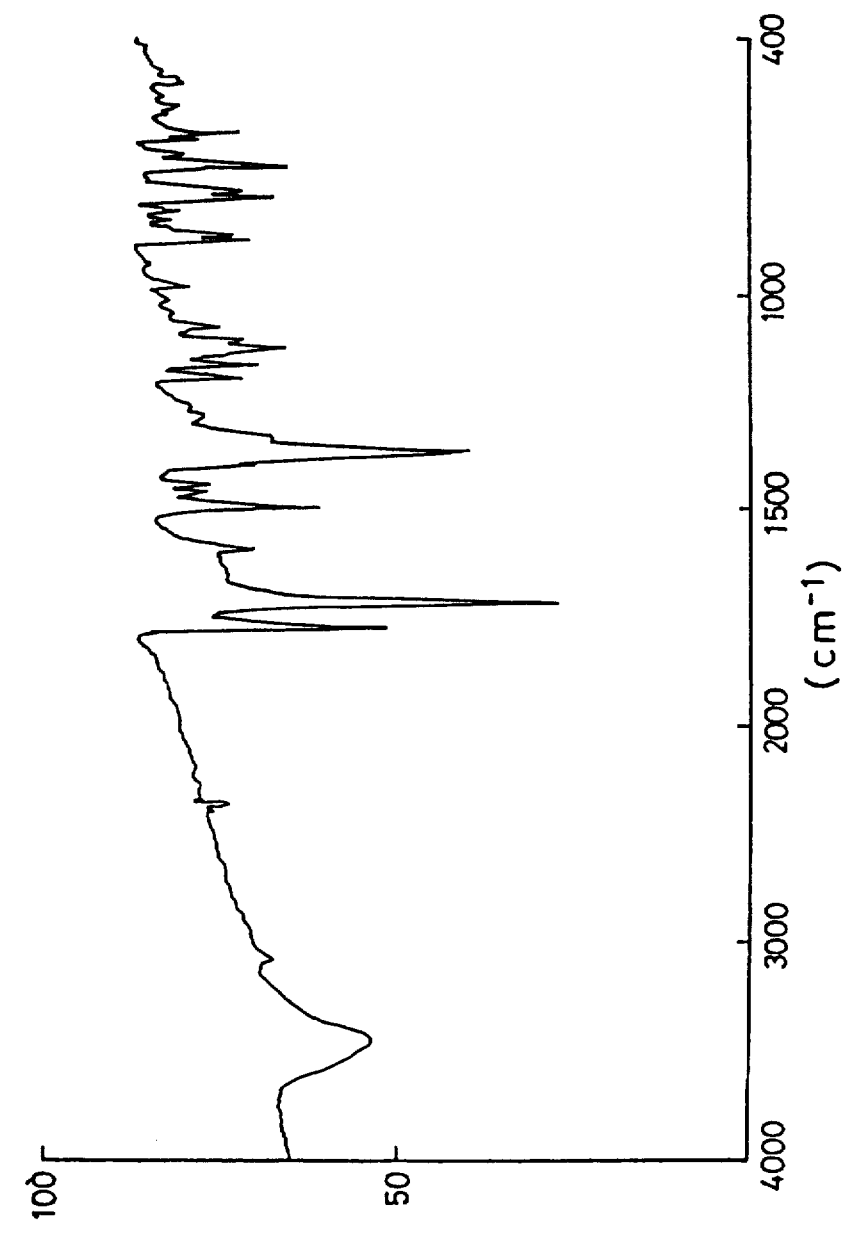
FIG. 8 is a method for pyrene compounds obtained in Example 7.
Figure 9:
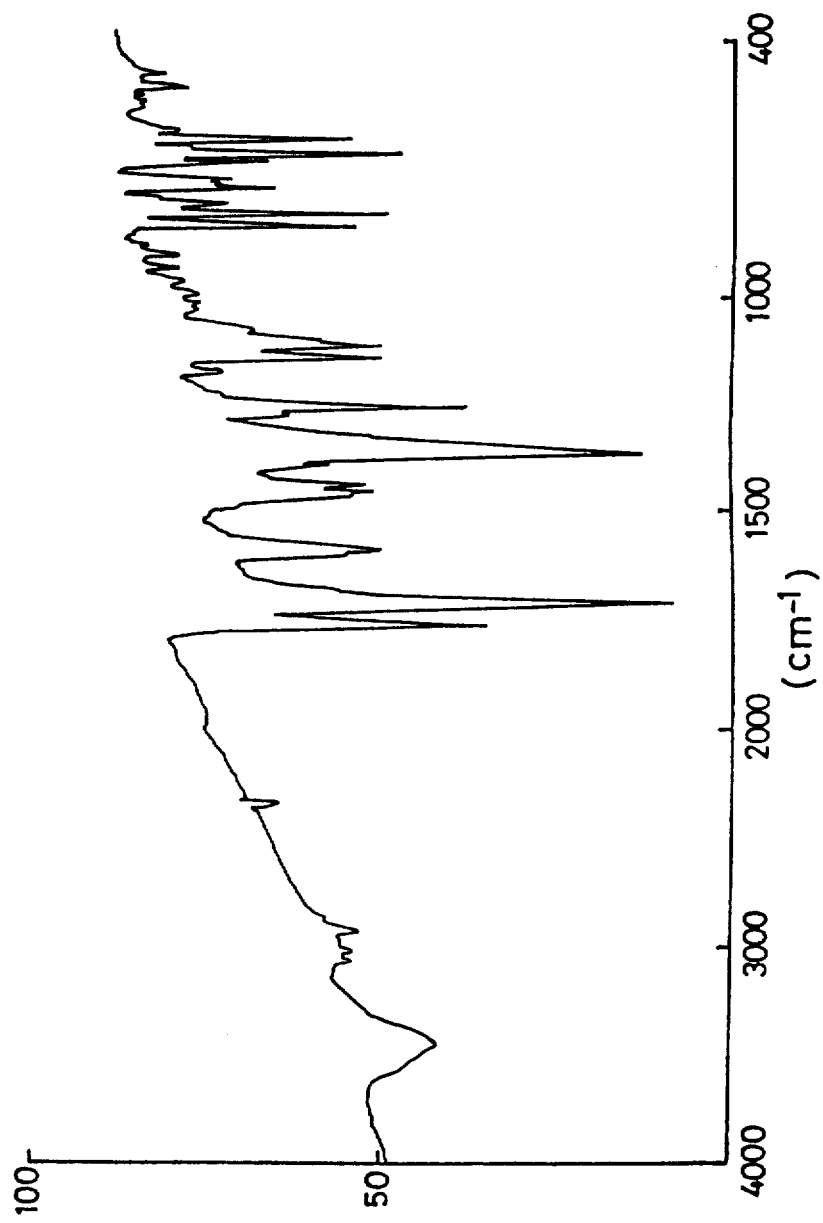
FIG. 9 is a diagram of infrared spectrum obtained through a KBr tablet method for pyrene compounds obtained in Example 8.
Figure 10:
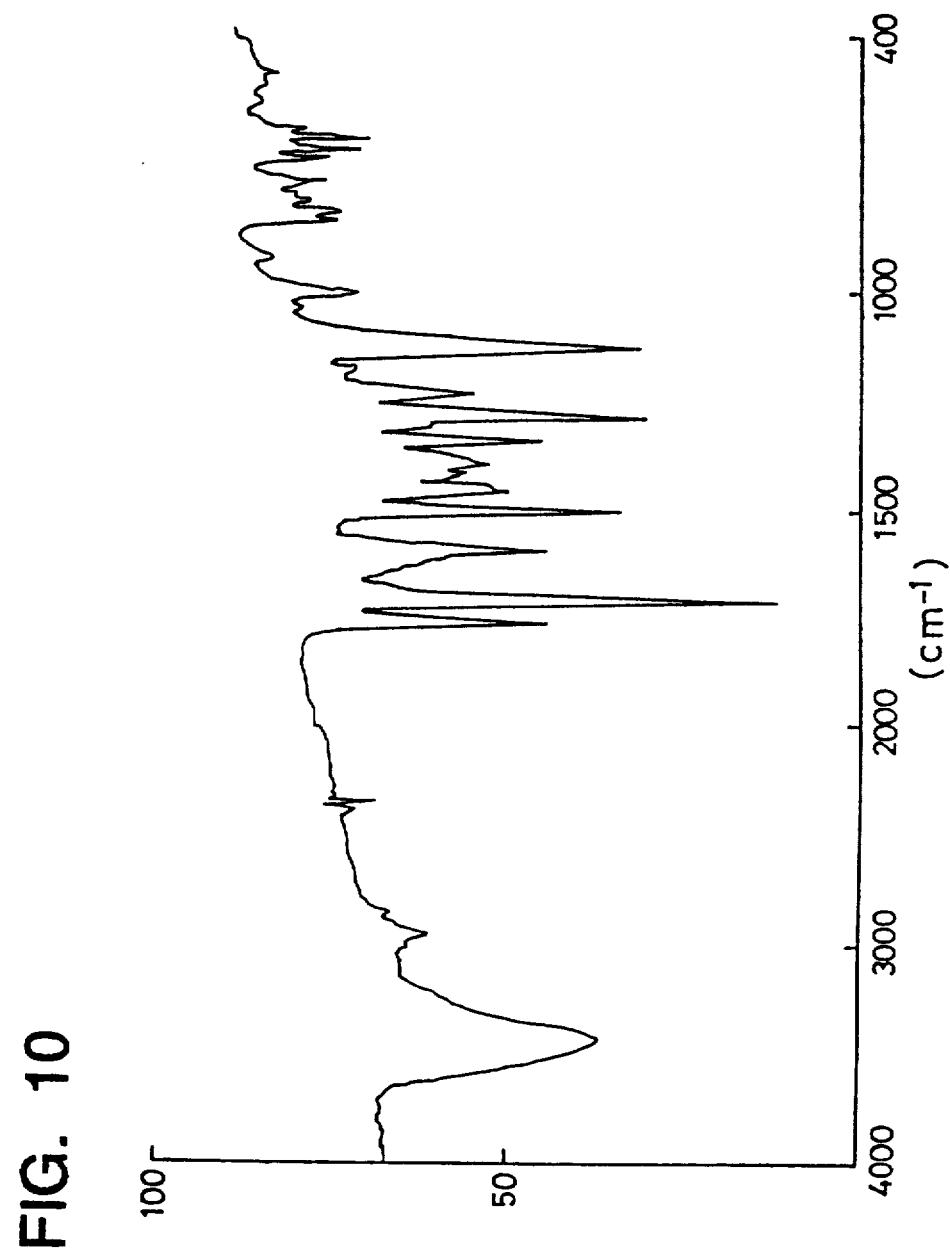
FIG. 10 is a diagram of infrared spectrum obtained through a KBr tablet method for pyrene compounds obtained in Example 9.
Figure 11:
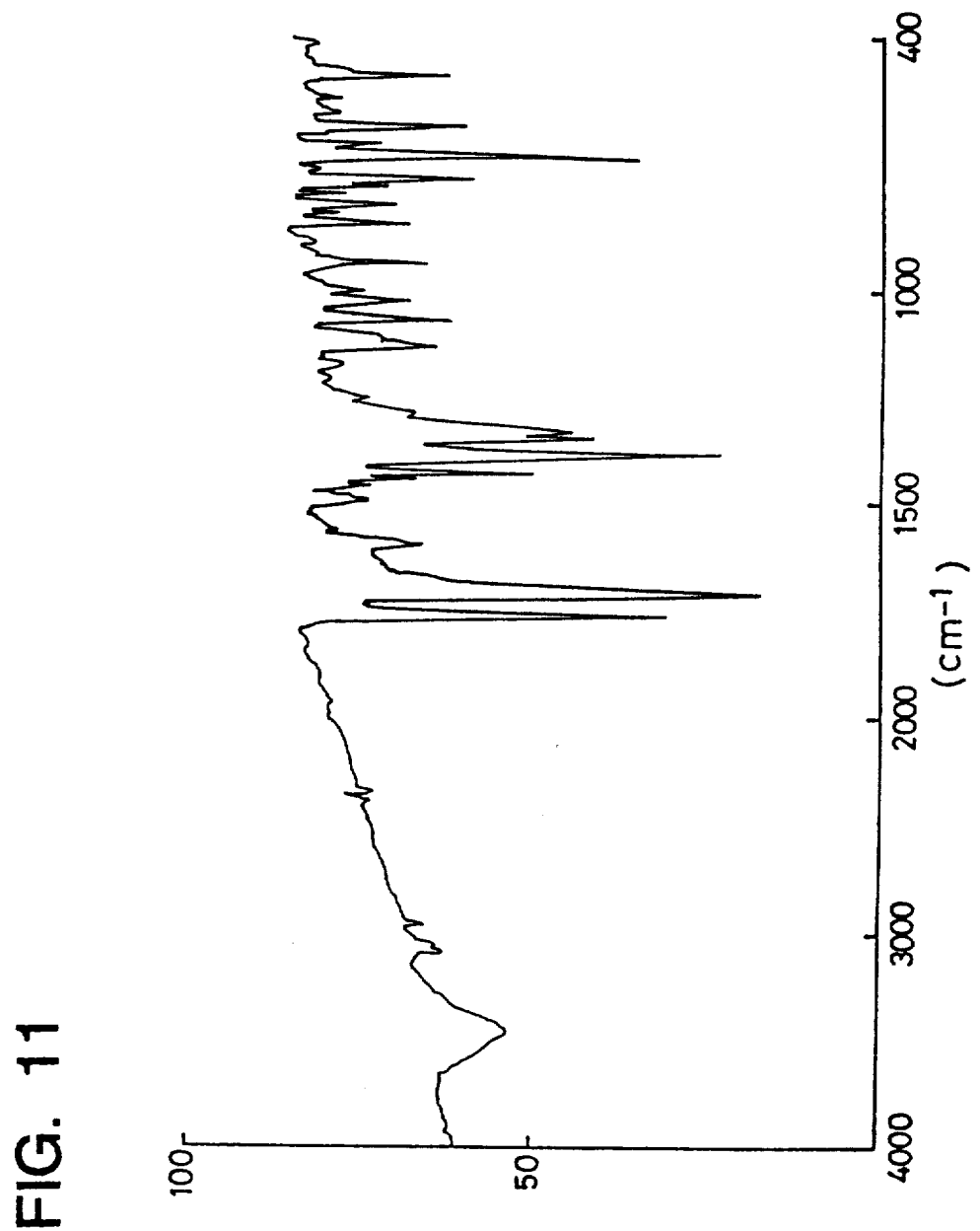
FIG. 11 is a diagram of infrared spectrum obtained through a KBr tablet method for pyrene compounds obtained in Example 10.

| Example No. | Amino compound | Pyrene compound No. | Yield (%) | Infrared absorption spectrum (KBr tablet method) |
|---|---|---|---|---|
| 6 | n-C$_3$H$_7$NH$_2$ | 124 | 82 | FIG. 7 |
| 7 | phenyl-NH$_2$ | 131 | 59 | FIG. 8 |
| 8 | 3,5-dimethylphenyl-NH$_2$ (CH$_3$, CH$_3$ substituted) | 134 | 93 | FIG. 9 |
| 9 | 3,4,5-trimethylphenyl-NH$_2$ (CH$_3$, CH$_3$, CH$_3$ substituted) | 139 | 95 | FIG. 10 |
| 10 | phenyl-CH$_2$CH$_2$- (2-phenylethyl amine) | 141 | 93 | FIG. 11 |

EXAMPLE 11

Pyrene compound of Compound No. 41 obtained in Example 1 was vacuum-evaporated to be a carrier-generating layer in thickness of 0.5 μm on an aluminum-vaporized polyester film On the carrier-generating layer, a liquid wherein 1 part of styryl compound represented by the following T-1, 1.3 parts of polycarbonate resin "INPILON Z-200" (made by MITSUBISHI GASU KAGAKU CO.) and infinitestimal silicone oil "KF-54" (made by SHIN-ETSU KAGAKU CO.) were dissolved as carrier-transport substances in 10 parts of 1,2-dichloroethane was coated by means of a blade type coater to form, after drying, a carrier-transport layer having a thickness of dried coating of 20 μm. The photoreceptor thus prepared was evaluated in the following manner by the use of a paper analizer EPA - 8100 (made by KAWAGUCHI DENKI CO.). At first, the photoreceptor was subjected to corona charging for 5 seconds at $-6$ kV, then its surface potential Va immediately after the charging and surface potential Vi after 5 seconds from the charging were obtained, and then the photoreceptor was subjected to exposure that caused the surface illumination intensity to be 8.2 lux. Exposure amount E$_\frac{1}{2}$ that is necessary to reduce the surface potential down to $\frac{1}{2}$ Vi and rate of dark decay D were obtained from an expression of D = 100 (Va−Vi)/Va. The results are shown in Table 3.

EXAMPLES 12-16

Photoreceptors were prepared in the same manner as in Example 11 except that pyrene compound of Compound No. 41 in Example 11 was replaced by pyrene compound in Table 3. The photoreceptors thus prepared were evaluated in the same manner as in Example 11. The results of them are shown in Table 3.

COMPARATIVE EXAMPLE (1)

Photoreceptors were prepared in the same manner as in Example 11 except that pyrene compound of Compound No. 41 in Example 11 was replaced by perynon compound represented by the following G - 1. The photoreceptors thus prepared were evaluated in the same manner as in Example 11. The results of them are shown in Table 3.

COMPARATIVE EXAMPLE (2)

Photoreceptors were prepared in the same manner as in Example 11 except that pyrene compound of Compound No. 41 in Example 11 was replaced by perynon compound represented by the following G - 2. The photoreceptors thus prepared were evaluated in the same manner as in Example 11. The results of them are shown in Table 3.

TABLE 3

(T-1)
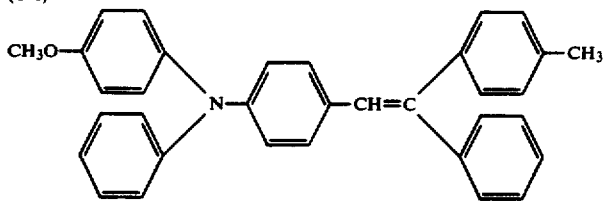

(G-1)
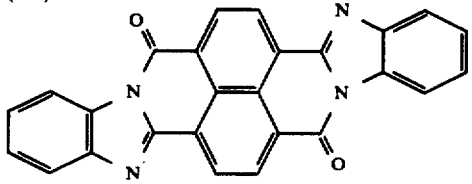

(G-2)
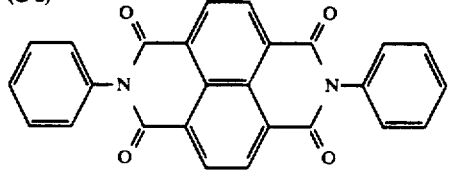

|  | Compound No. | $V_a$ (V) | $E_{\frac{1}{2}}$ (lux · sec) | DD (%) |
|---|---|---|---|---|
| Example 11 | 41 | −1010 | 2.1 | 13.1 |
| Example 12 | 42 | −1050 | 2.3 | 11.8 |
| Example 13 | 51 | −1170 | 2.7 | 15.3 |
| Example 14 | 131 | −1110 | 3.9 | 11.3 |
| Example 15 | 134 | −1030 | 3.0 | 16.8 |
| Example 16 | 141 | −1020 | 3.2 | 15.3 |
| Comparative example (1) | G-1 | −970 | 4.5 | 18.3 |
| Comparative example (2) | G-2 | −1050 | 10.4 | 14.0 |

Pyrene compounds of the invention may be manufactured easily and are useful as a photoconductive compound as is clearly shown by the examples.

What is claimed is:

1. A photoreceptor, comprising at least one of pyrene compounds represented by following general formula (1), (2), (3), (4) and (5):

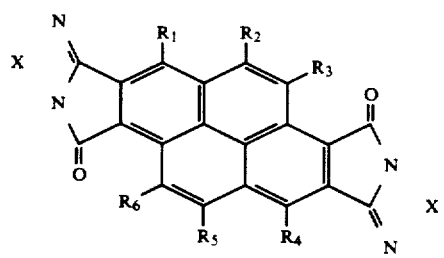

Formula (1)

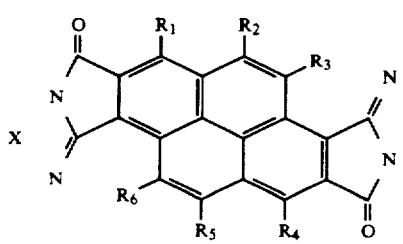

Formula (2)

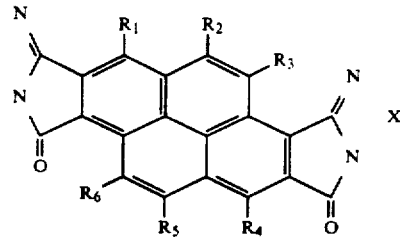

Formula (3)

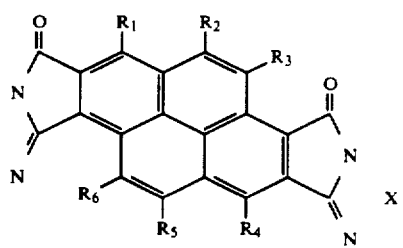

Formula (4)

wherein X represents a substituted or unsubstituted divalent aromatic ring, and $R_1$-$R_6$ each represents a hydrogen atom, a halogen atom, an alkyl group, an alkoxy group, an aryloxy group, an aralkyl group, or a substituted or unsubstituted aromatic group.

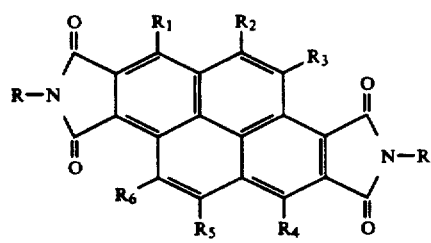

Formula (5)

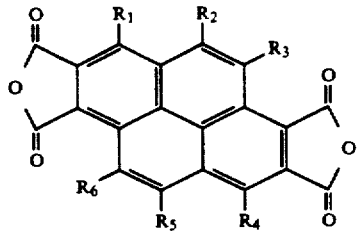

Formula (6)

wherein R represents a hydrogen atom, a halogen atom, a substituted or unsubstituted alkyl group, or a substituted or unsubstituted aromatic residue, and $R_1$-$R_6$ each represents a hydrogen atom, a halogen atom, an alkyl group, an alkoxy group, an aryloxy group, an aralkyl group, or a substituted or unsubstituted aromatic group.

2. The photoreceptor of claim 1, wherein the photoreceptor comprises one of pyrene compounds represented by the formulas (1), (2), (3) and (4).

3. The photoreceptor of claim 2, wherein X is selected from the groups containing of a benzene ring, a naphthalene ring, an anthracene ring, a phenanthrene ring, a pyridine ring, a pyrimidine ring and an anthraquinone ring.

4. The photoreceptor of claim 3, wherein X represents a benzene ring or a naphthalene ring.

5. The photoreceptor of claim 2, wherein X is a unsubstituted divalent aromatic ring.

6. The photoreceptor of claim 2, wherein a substituent of X includes an alkyl, alkoxy, aryl, aryloxy, acyl, acyloxy, amino, carbamoyl, halogen, nitro, and cyano group.

7. The photoreceptor of claim 2, wherein $R_1$ and $R_4$ each represents a substituted or unsubstituted aromatic group, and $R_2$, $R_3$, $R_5$, and $R_6$ each represents a hydrogen atom or a halogen atom.

8. The photoreceptor of claim 2, wherein the pyrene compounds represented by formulas (1), (2), (3) and (4) are manufactured through dehydration condensation reaction between pyrene-1,2,6,7-tetracarboxylic anhydride represented by formula (6) or its derivative and a diamino compound represented by formula (7)

wherein $R_1$-$R_6$ in formula (1), (2), (3) and (4) are used $R_1$-$R_6$ in formula (6)

Formula (7)

wherein X in formula (1), (2), (3) and (4) are used for X in formula (7).

9. The photoreceptor of claim 2, wherein the pyrene compound represented by formula (5) is manufactured through dehydration condensation reaction between pyrene-1,2,6,7-tetracarboxylic anhydride represented by formula (6) or its derivative and an amino compound represented by formula (8)

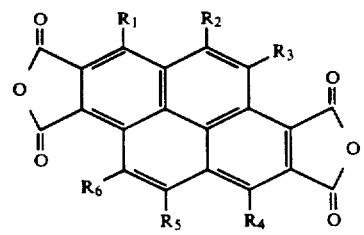

Formula (6)

wherein $R_1$-$R_6$ in formula (1), (2), (3) and (4) are used for $R_1$-$R_6$ in formula (6)

R—$NH_2$   Formula (8)

wherein R in formula (5) is used for R in formula (8).

* * * * *

UNITED STATES PATENT AND TRADEMARK OFFICE
CERTIFICATE OF CORRECTION

PATENT NO. : 5,294,512
DATED : March 15, 1994
INVENTOR(S) : Tomoko SUZUKI et al.

Page 1 of 2

It is certified that error appears in the above-indentified patent and that said Letters Patent is hereby corrected as shown below:

Claim 1, column 57, lines 50-68 and column 58 lines 43-63, Formulas 1-4, change

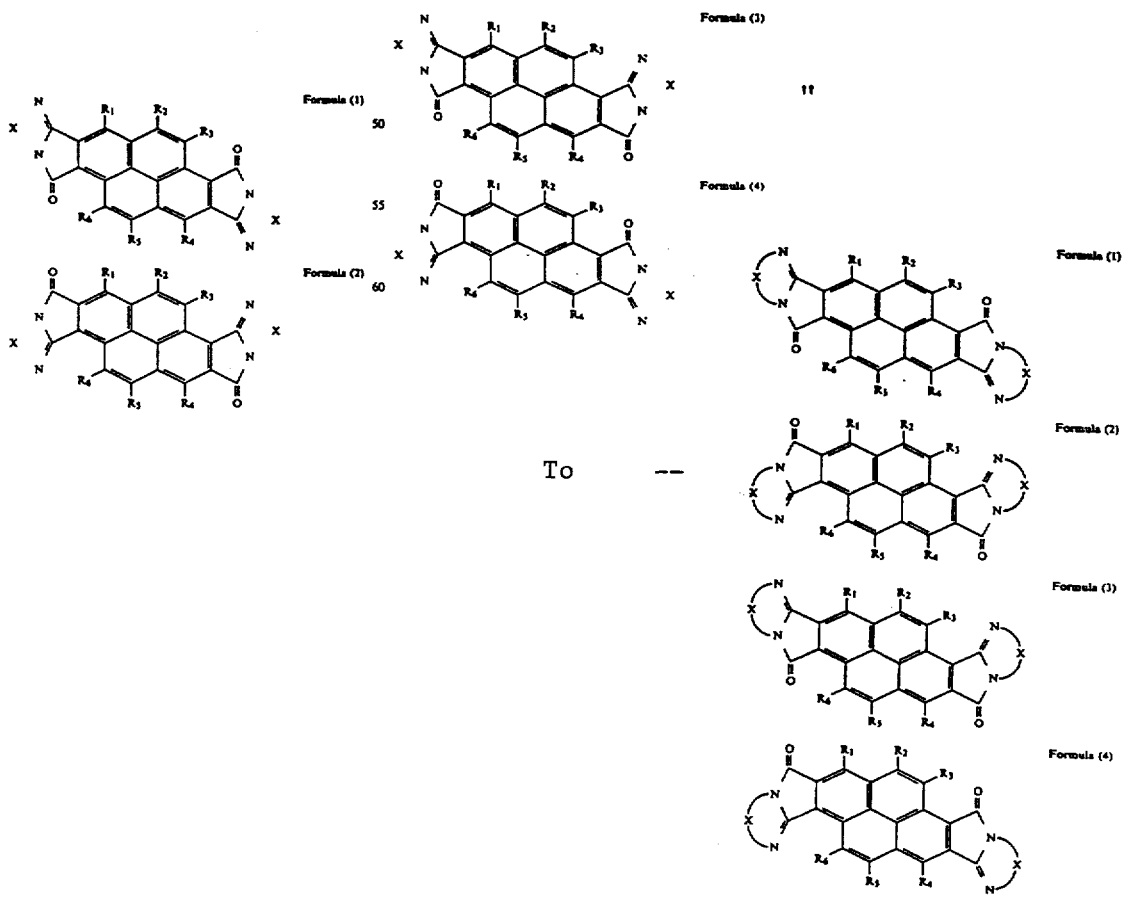

UNITED STATES PATENT AND TRADEMARK OFFICE
CERTIFICATE OF CORRECTION

PATENT NO. : 5,294,512
DATED : March 15, 1994
INVENTOR(S) : Tomoko SUZUKI et al.

It is certified that error appears in the above-indentified patent and that said Letters Patent is hereby corrected as shown below:

Claim 3, column 59, line 23 change "containing" to --consisting--.

Signed and Sealed this

Seventh Day of March, 1995

Attest:

BRUCE LEHMAN

Attesting Officer    Commissioner of Patents and Trademarks